(12) United States Patent
Narine et al.

(10) Patent No.: US 9,434,674 B2
(45) Date of Patent: Sep. 6, 2016

(54) LATENT HEAT STORAGE USING RENEWABLE PHASE CHANGE MATERIALS

(71) Applicant: Trent University, Peterborough (CA)

(72) Inventors: Suresh S. Narine, Peterborough (CA); Michael C. Floros, Aurora (CA)

(73) Assignee: Trent University, Peterborough (CA)

( * ) Notice: Subject to any disclaimer, the term of this patent is extended or adjusted under 35 U.S.C. 154(b) by 0 days.

(21) Appl. No.: 14/605,344

(22) Filed: Jan. 26, 2015

(65) Prior Publication Data

US 2016/0214921 A1    Jul. 28, 2016

(51) Int. Cl.
*C11C 3/00* (2006.01)
*C07C 67/03* (2006.01)

(52) U.S. Cl.
CPC ................................. *C07C 67/03* (2013.01)

(58) Field of Classification Search
CPC ...................................................... C07C 67/03
USPC ......................................................... 554/163
See application file for complete search history.

(56) References Cited

U.S. PATENT DOCUMENTS

| | | | |
|---|---|---|---|
| 4,976,892 A | 12/1990 | Jeromin et al. | |
| 5,501,268 A | 3/1996 | Stovall et al. | |
| 5,648,483 A | 7/1997 | Granberg et al. | |
| 2006/0233986 A1 | 10/2006 | Gutsche et al. | |
| 2011/0124769 A1 | 5/2011 | Moen et al. | |
| 2012/0259087 A1* | 10/2012 | Cramail | C07D 317/36 528/229 |
| 2012/0260656 A1 | 10/2012 | Tseng et al. | |
| 2012/0283467 A1* | 11/2012 | Cramail | C08G 18/3865 560/154 |
| 2013/0056175 A1 | 3/2013 | Hidalgo et al. | |

FOREIGN PATENT DOCUMENTS

CN      103360243 A  * 10/2013
WO      WO 01/99871     8/2011

OTHER PUBLICATIONS

Maisonneuve et al,, Polym. Chem. 2012, 3,25 83-2595.*
Abes et al., Crystallization and phase behavior of fatty acid esters of 1,3-propanediol I: Pure systems, Chemistry and Physics of Lipids, vol. 149, 2007, pp. 14-27.
Abes et al., Crystallization and phase behavior of 1,3-propanediol esters II. 1,3-Propanediol distearate/1,3-propanediol diplamitate (SS/PP) and 1,3-propanediol distearate/1,3-propanediol dimyristate (SS/MM) binary systems, Chemistry and Physics of Lipids, vol. 150, 2007, pp. 89-108.
Abes et al., Crystallization and phase behavior of fatty acide esters of 1,3 propanediol III: 1,3 propanediol dicaprylate/1,3 propanediol distearate (CC/SS) and 1,3 propanediol dicaprylate/1,3 propanediol dipalmitate (CC/PP) binary systems, Chemistry and Physics of Lipids, vol. 151, 2008, pp. 110-124.
Alkan et al., Preparation and thermal properties of ethylene glycol distearate as a novel phase change material for energy storage, Materials Letters, vol. 62, 2008, pp. 1122-1125.

(Continued)

*Primary Examiner* — Deborah D Carr
(74) *Attorney, Agent, or Firm* — Foley & Lardner LLP

(57) ABSTRACT

A method of producing a diol diester, which includes reacting a fatty acid alkyl ester having 6 to 30 carbon atoms, an α,ω-alkanediol having n carbon atoms, wherein n is an integer from 2 to 22; and a basic transesterification catalyst, is provided. Use of the diol diesters as phase change materials is also provided.

26 Claims, 1 Drawing Sheet

(56) References Cited

OTHER PUBLICATIONS

Ataya et al., Acid-catalyzed transesterification of canola oil to biodiesel under single- and two-phase reaction conditions, Energy & Fuels 21(4), 2007, pp. 2450-2459.

Aydin, A. A., Fatty acid ester-based commercial products as potential new phase change materials (PCMB) for thermal energy storage, Solar Energy Materials and Solar Cells, vol. 108, 2013, pp. 98-104.

Cabeza et al., Materials used as PCM in thermal energy storage buildings: a review, Renewable and Sustainable Energy Reviews 15(3), 2011, pp. 1675-1695.

Farid et al., A review on phase change energy storage: materials and applications, Energy conversion and management 45(9), 2004, pp. 1597-1615.

Feldman et al., Low chain esters of stearic acid as phase change materials for thermal energy storage in buildings, Solar Energy Materials and Solar Cells 36(3), 1995, pp. 311-322.

Floros et al., Saturated linear diesters from stearic acid as renewable phase change materials, Materials Letters, vol. 137, 2014, pp. 252-255.

Hasnain, S. M., Review on sustainable thermal energy storage technologies, Part I: Heat storage materials and techniques, Energy Conversion and Management 39(11), 1998, pp. 1127-1138.

He et al., Technical grade paraffin waxes as phase change materials for cool thermal storage and cool storage systems capital cost estimation, Energy Conversion and Management 43(13), 2002, pp. 1709-1723.

Hoshi et al., Screening of high melting point phase change materials (PCM) in solar thermal concentrating technology based on CLFR, Solar Energy 79(3), 2005, pp. 332-339.

Khudhair et al., A review on energy conservation in building applications with thermal storage by latent heat using phase change materials, Energy Conversion and Management 45(2), 2004, pp. 263-275.

Li et al., Preparation and characterization of a novel solid-liquid PCM: Butanediol di-stearate, Materials Letters, vol. 61, 2007, pp. 1526-1528.

Li et al., Preparation and characterization of a series of diol di-stearates as phase change heat storage materials, Materials Letters, vol. 61, 2007, pp. 4325-4328.

Noureddini, Glycerolysis of Fats and Methyl Esters, JAOCS 74(4), 1997, 8 pages.

Noureddini et al, Kinetics of Transesterification of Soybean Oil, JAOCS 74(11), pp. 1457-1463.

Sarier et al., The manufacture of microencapsulated phase change materials suitable for the design of thermally enhanced fabrics, Thermochimica Acta 452(2), 2007, pp. 149-160.

Sarier et al., Organic phase change materials and their textile applications: An overview, Thermochimica Acta, vol. 540, 2012, pp. 7-60.

Sonntag, N., Glycerolysis of Fats and Methyl Esters-Status, Review and Critique, JAOCS 59(10), 1982, pp. 795A-802A.

von Wilhelm Schlenk jr., Melting Points in Homologous Series of Long-Chain Compounds, Justus Liebigs Annalen der Chemie, vol. 727, 1969, pp. 1-9.

Maisonneuve et al., Hydroxyl telechelic building blocks from fatty acid methyl esters for the synthesis of poly(ester/amide urethane)s with versatile properties, Polym. Chem., 2012, vol. 3, pp. 2583-2595, 14 pages.

Schuchardt et al., Transesterification of Vegetable Oils: a Review, J. Braz. Chem. Soc., 1998, vol. 9, No. 1, pp. 199-210.

International Search Report and Written Opinion regarding International Appl. No. PCT/IB2016/050112, mail date Mar. 23, 2016, 14 pages.

\* cited by examiner

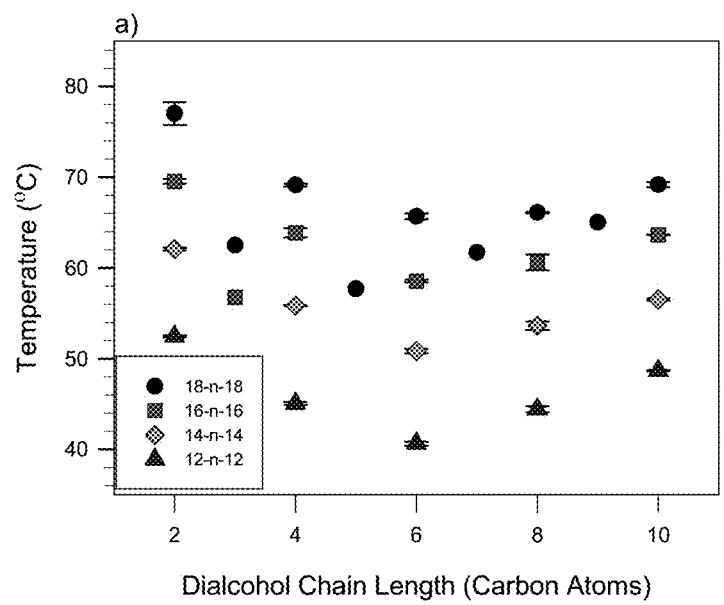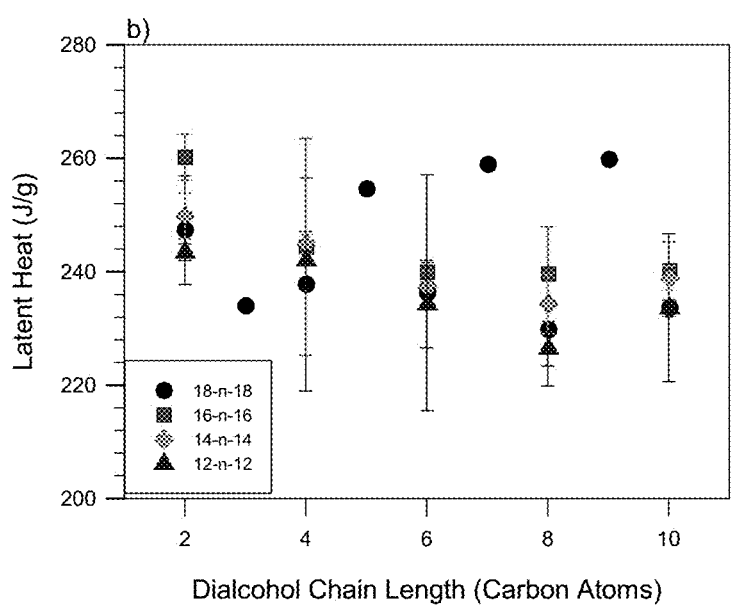

LATENT HEAT STORAGE USING RENEWABLE PHASE CHANGE MATERIALS

BACKGROUND

Phase change materials (PCMs) are used to store and release thermal energies through phase transformations—most commonly melting and crystallization. The energy which is stored and released in these transitions is known as latent heat, and latent heat storage is among the most effective techniques for storing thermal energy.

In commercial and industrial settings, several distinct classes of PCMs are used for heat storage. Different temperature ranges between the classes of PCMs generally dictates which type of PCM will be suitable for a specific application. PCMs are most often divided into classifications based on their chemical composition. Inorganic PCMs such as hydrated and molten salts are commonly used for high temperature applications, while organic PCMs such as fatty acids and paraffin waxes are used at lower temperatures. Paraffin waxes are one of the most widely used PCMs. The melting point of a paraffin wax is dependent on the number of carbon atoms in the paraffin and generally increases with the average carbon number.

Due to the environmental implications and increasing economic costs associated with limited oil reserves and corresponding increasing costs associated with petrochemicals, renewable alternatives for paraffin wax are attracting significant attention. Analysis of the constituents of paraffin waxes in candles shows that they also contain hazardous materials such as toluene, trichloroethylene, and a variety of alkanes and alkenes, many of which have unknown safety implications. Due to these toxicity issues and the non-renewability of the feedstock, interest and demand for other types renewable PCMs has been growing. Fatty acid derived materials are suitable candidates for the substitution of paraffin wax in many applications—they may be non-toxic, are renewable, and are less corrosive than inorganic PCMs. However, the fatty acid derived PCMs produced to date have melting temperature and latent heat values lower than those of paraffin wax, resulting in lower energy storage densities. For example, triglycerides have been transesterified with a short chain alcohol to create fatty acid alkyl esters for use as PCMs. In such applications, modifications of the feedstock's oil or hydrogenation of the double bond was reported to provide blends of fatty esters with varying melting points and latent heat values between 110-140 J/g. Although the PCMs that were produced are derived from renewable feedstocks, the melting points and latent heat values compare unfavorably with paraffins. Thus, use of these fatty acid alkyl ester PCMs would require a significantly larger PCM mass to store the same amount of thermal energy as paraffin waxes, which have been reported to have latent heats between about 146-210 J/g.

SUMMARY

The present disclosure provides a synthesis of diol diester compounds from fatty acids or fatty acid derivatives and dialcohols ("diols"), such as alkanediols. The application also provides the use of such materials as PCMs or latent heat energy storage materials, e.g., for use in thermal energy storage and temperature regulation applications.

In one aspect, a method of producing a diol diester is provided. The method includes reacting a fatty acid alkyl ester having 6 to 30 carbon atoms, an $\alpha,\omega$-alkanediol having n carbon atoms, wherein n is an integer from 2 to 22, and about 0.01 to 1.0 wt. % (based on the weight of the mixture) of a basic transesterification catalyst, wherein the mixture is reacted at a reaction temperature of at least about 60° C. to provide a first reaction product comprising the diol diester. The fatty acid alkyl ester may include a fatty acid methyl ester having 7 to 23 carbon atoms, the $\alpha,\omega$-alkanediol may include 2 to 22 carbon atoms, and the basic transesterification catalyst may include an alkali metal hydroxide and/or alkali metal carbonate. The fatty acid alkyl ester may include one or more saturated fatty acid methyl esters or one or more unsaturated fatty acid methyl esters.

In another aspect, a method of producing a diol ester compound in a single stage reaction is provided. The method includes reacting a mixture including a lower alkyl ester of an aliphatic carboxylic acid or an alkanedicarboxylic acid lower alkyl diester, with an $\alpha,\omega$-alkanediol wherein one more methylene subunits may be substituted by an oxygen atom (e.g., a polyalkylene glycol, such as a polyethylene glycol), and a transesterification catalyst. The mixture is typically reacted at a reaction temperature which is at least about 20° C. higher than the highest of (1) the melting point of the diol ester compound, (2) the melting point of the aliphatic carboxylic acid lower alkyl ester (or alkanedicarboxylic acid lower alkyl diester) and (3) the boiling point of a lower alkanol corresponding to the lower alkyl group of the ester group. Where the reactants are an aliphatic carboxylic acid lower alkyl ester and an $\alpha,\omega$-alkanediol (or oxygenated analog thereof), the reaction product is a diol diester.

In one aspect, a latent heat storage article is provided including a matrix material having a phase change material (PCM) embedded therein, wherein the PCM includes a diol diester having a melting point of about 30 to 90° C. and represented by a formula

$$R-C(O)O-(CH_2)_n-OC(O)-R'$$

wherein the R—C(O)O— and R'—C(O)O— groups are fatty acid acyl groups and the R— and R'— groups independently have from 5 to 30 carbon atoms (commonly about 10 to 18); and n is an integer from 2 to 22 (commonly about 2 to 15). The diol diester may include fatty acid acyl groups corresponding to the fatty acid composition of a fatty acid ester material, such as a natural triacylglyceride material (e.g., tallow or a vegetable oil) or fraction thereof.

BRIEF DESCRIPTION OF THE DRAWINGS

FIG. 1 shows graphs depicting 1(a) peak melting point of a series of diol diesters of even carbon length saturated fatty acids and 1(b) latent heat values for the same series of diol diesters. All values are single replicates except for the 18-n-18 series, which shows the average values, where the error bars represent standard deviations from duplicates or triplicates.

DETAILED DESCRIPTION

The present disclosure provides methods for producing diol diester PCMs having greater enthalpy of crystallization and higher melting temperatures than conventionally produced PCMs. The method includes reacting a fatty acid alkyl ester with an alkanediol, typically an $\alpha,\omega$-alkanediol, optionally in the presence of a catalyst, to provide a first reaction product comprising the diol diester.

In some embodiments, the $\alpha,\omega$-alkanediol is linear or branched alkanediol having n carbon atoms, wherein n is an integer from 2 to 22 carbon atoms. This includes from 2 to 20 carbon atoms, from 2 to 15 carbon atoms, from 2 to 12 carbon atoms or from 2 to 4 carbon atoms. Suitable α,ω-alkanediols include, for example, ethanediol, 1,3-propanediol, 1,4-butanediol, 1,5-pentanediol, 1,6-hexanediol, 1,7-heptanediol, 1,8-octanediol, 1,9-nonanediol, 1,10-decanediol, 1,12-dodecanediol, 1,16-hexadecanediol, 2-methyl-1,4-butanediol, 2-ethyl-1,4-butanediol, 2-propyl-1,4-butanediol, 2-chloro-1,4-butanediol, 2-methyl-1,5-pentanediol, 3-methyl-1,5-pentanediol, 3-ethyl-1,6-hexanediol, 3-propyl-1,6-hexanediol, and the like or a combination of any two or more thereof. In some embodiments, the α,ω-alkanediol includes ethanediol, 1,3-propanediol and/or 1,4-butanediol. In some embodiments, the α,ω-alkanediol is 1,4-butanediol. In other embodiments, the α,ω-alkanediol is ethanediol. In some embodiments, the α,ω-alkanediol may have one more methylene subunits substituted by an oxygen atom (e.g., a polyalkylene glycol, such as a polyethylene glycol).

In some embodiments, the fatty acid alkyl ester (FAAE) has from about 4 to about 40 carbon atoms. This includes fatty acid alkyl esters having from about 6 to about 30 carbon atoms, from about 8 to about 25 carbon atoms, from about 10 to about 22 carbon atoms, from about 11 to about 19 carbon atoms, or from about 15 to about 19 carbon atoms.

In some embodiments, the FAAE is an alkyl ester of a aliphatic carboxylic acid having from about 6 to about 30 carbon atoms. This includes carboxylic acids having from about 6 to about 22 carbon atoms, from 8 to 18 carbon atoms, from 10 to 18 carbon atoms, from 14 to about 18 carbon atoms, or 16 and/or 18 carbon atoms. Suitable carboxylic acids include short chain fatty acids, medium chain fatty acids and long chain fatty acids. The acids may be linear or branched, saturated or unsaturated, monofunctional or polyfunctional. In some embodiments, the carboxylic acid(s) includes one or more saturated fatty acids. In other embodiments, the carboxylic acid(s) includes one or more unsaturated fatty acids.

In some embodiments, the FAAE is a lower alkyl ester of a fatty acid As used herein, the term "lower alkyl" is an alkyl having 1 to 6 carbon atoms. Commonly, the lower alkyl group has 1 to 4 carbon atoms, or 1 to 2 carbon atoms. In some embodiments, the fatty acid ester is a methyl, ethyl, propyl, or butyl ester of a fatty acid, such as caproic acid, caprylic acid, 2-ethylhexanoic acid, capric acid, lauric acid, isotridecanoic acid, myristic acid, myristoleic acid, palmitic acid, palmitoleic acid, vaccenic acid, paulinic acid, stearic acid, isostearic acid, sapienic acid, oleic acid, elaidic acid, vaxxenic acid, petroselic acid, linoleic acid, linolenic acid, elaeostearic acid, arachic acid, archidonic acid, eicosapentaenoic acid, gadoleic acid, behenic acid, cerotic acid and erucic acid, nervonic acid, mead acid and docosahexaenoic acid, and the like, or a combination of any two or more thereof. In some embodiments, the fatty acid has an even number of carbon atoms. In some embodiments, the fatty acid has an odd number of carbon atoms.

In some embodiments, the FAAE includes a lower alkyl ester of a saturated fatty acid. In other embodiments, the FAAE includes a lower alkyl ester of an unsaturated fatty acid. This includes for example methyl ester, ethyl ester, propyl ester, or butyl ester. In some embodiments, the FAAE is a methyl ester of one or more fatty acids (FAME). In some embodiments, the FAAE includes one or more saturated FAME. In some embodiments, the FAAE includes methyl stearate, methyl palmitate, methyl methyl myristate, or methyl laurate, or a combination of two or more thereof. In some embodiments, the FAAE is methyl stearate. In other embodiments, the FAAE is methyl palmitate. In some embodiments, the FAAE includes methyl stearate and methyl palmitate. In some embodiments, the FAAE includes one or more unsaturated FAME. In some embodiments, the FAAE includes methyl oleate. In some embodiments, the fatty acid alkyl ester is a methyl ester of a fatty acid having an even number of carbon atoms.

In some embodiments, the fatty acid alkyl ester and the α,ω-alkanediol are added to the reaction mixture in a mole ratio of about 1:1 to 10:1. This includes a mole ratio or about 2:1, about 2.1:1, about 2.2:1, about 2.5:1, about 3:1, about 5:1 or about 8:1, of fatty acid alkyl ester and α,ω-alkanediol, respectively. Quite commonly, the fatty acid alkyl ester and the α,ω-alkanediol are reacted in a mole ratio of about 2:1 to 2.2:1, and often 2:1 to 2.1:1.

In some embodiments, the reaction mixture including the fatty acid alkyl ester and the α,ω-alkanediol is substantially free of solvent, i.e., the mixture contains less than about 5 wt. % and more commonly less than about 1 wt. % solvent. Quite often the reaction mixture does not include any solvent ("solvent-free").

In some embodiments, the FAAE and α,ω-alkanediol are reacted in the presence of a suitable catalyst, for example a transesterification catalyst. The catalyst may be a basic transesterification catalyst. In some embodiments, the basic transesterification catalyst is an inorganic basic compound. Suitable inorganic basic compounds include alkali metals, alkali metal carbonates, alkaline earth carbonates, alkali metal hydrides, alkaline earth hydrides, alkali metal alkoxides, and alkaline earth alkoxides, and the like or a combination of any two or more thereof. In some embodiments, the basic transesterification catalyst includes an alkali metal hydroxide, such as sodium methoxide and/or potassium methoxide. The basic transesterification catalyst may include an alkali metal alkoxide and/or alkali metal carbonate. In some embodiments, the basic transesterification catalyst includes an alkali metal hydroxide and/or alkali metal carbonate. In some embodiments, the basic transesterification catalyst is selected from sodium hydroxide, sodium carbonate, potassium hydroxide and potassium carbonate. In some embodiments, the basic transesterification catalyst includes potassium hydroxide. In other embodiments, the basic transesterification catalyst includes potassium carbonate.

In some embodiments, the fatty acid alkyl ester is a fatty acid methyl ester having 7 to 23 carbon atoms, the α,ω-alkanediol has 2 to 22 carbon atoms, and the basic transesterification catalyst includes an alkali metal hydroxide and/or alkali metal carbonate, typically potassium hydroxide and/or potassium carbonate. In other embodiments, the fatty acid alkyl ester is a fatty acid methyl ester having 11 to 19 carbon atoms, the α,ω-alkanediol has 2 to 12 carbon atoms, and the basic transesterification catalyst comprises an alkali metal hydroxide and/or alkali metal carbonate.

In some embodiments, the mixture of FAAE and α,ω-alkanediol is reacted at a reaction temperature of at least about 40° C. This includes a reaction temperature of at least about 50° C., at least about 60° C., at least about 70° C., at least about 80° C., and at least about 90° C. In some embodiments, the mixture of FAAE and α,ω-alkanediol is reacted at a reaction temperature of at least about 90° C. In some embodiments, the mixture of FAAE and α,ω-alkanediol is reacted at a reaction temperature of from about 40° C. to about 200° C., from about 50° C. to about 180° C., from about 60° C. to about 200° C., from about 90° C. to about 150° C., or from about 100° C. to about 130° C. In some embodiments, the mixture of FAAE and α,ω-alkanediol is reacted at a reaction temperature of at least about 60° C. In some embodiments, the mixture of FAAE and α,ω-alkanediol is reacted at a reaction temperature of from about 60° C. to about 200° C. In other embodiments, the mixture of FAAE and α,ω-alkanediol is reacted at a reaction temperature of from about 90° C. to about 150° C. In some embodiments, the FAAE is a fatty acid methyl ester, and the method includes reacting the mixture of FAAE and α,ω-alkanediol at a temperature of about 90° C. to 150° C.

The reaction temperature may also be modulated to be chosen in relation to the melting/boiling points of the reactants and/or the products. Thus, in one embodiment, the reaction mixture may be reacted at a reaction temperature which is higher than the highest of (1) the melting point of the diol diester reaction product, (2) the melting point of the aliphatic carboxylic acid lower alkyl ester and (3) the boiling point of a lower alkanol corresponding to the lower alkyl ester. In some embodiments, the reaction mixture is reacted at a reaction temperature which is at least about 10° C. higher, at least about 15° C. higher, at least about 20° C. higher, at least about 25° C. higher, at least about 30° C. higher, or at least about 40° C. higher, than the highest of (1) the melting point of the diol diester, (2) the melting point of the aliphatic carboxylic acid lower alkyl ester and (3) the boiling point of a lower alkanol corresponding to the lower alkyl ester.

As noted above, the mixture of FAAE and α,ω-alkanediol is commonly reacted at a reaction temperature of no more than about 200° C. The upper limit of the reaction temperature may be modulated to be chosen in relation to the boiling points of certain of the reactants and/or the degradation temperature of the reaction product(s). Typically the reaction of the mixture is conducted at a temperature which is at least about 10° C. lower, at least about 15° C. lower, at least about 20° C. lower, at least about 25° C. lower, at least about 30° C. lower, or at least about 40° C. lower than the lowest of (1) the boiling point of the aliphatic carboxylic acid lower alkyl ester and (2) the boiling point of the diol.

In one aspect, provided is a method of producing a diol diester in a single stage reaction including reacting a mixture which includes a lower alkyl ester of an aliphatic carboxylic acid or an alkanedicarboxylic acid lower alkyl diester, an α,ω-alkanediol wherein one more methylene subunits may be substituted by an oxygen atom, and a transesterification catalyst. The reaction is typically conducted at a reaction temperature which is at least about 20° C. higher than the highest of (1) the melting point of the diol diester, (2) the melting point of the aliphatic carboxylic acid lower alkyl ester (or alkanedicarboxylic acid lower alkyl diester) and (3) the boiling point of a lower alkanol corresponding to the lower alkyl ester. In some embodiments, the lower alkyl ester of an aliphatic carboxylic acid includes C1-C6 alkyl carboxylic acid esters, e.g., methyl or ethyl esters. In some embodiments, the α,ω-alkanediol is linear or branched alkanediol having n carbon atoms, wherein n is an integer from 2 to 22 carbon atoms. An embodiment of a solvent free, melt transesterification method for producing fatty acid derived diesters directly from FAME and short chain dialcohols in a single step using a small quantity of a basic catalyst, is illustrated in Scheme I. In the scheme illustrated in Scheme I, R is an alkylene chain, typically 2 to 10 carbons in length, and R' is a fatty acid group, typically of 7 to 21 carbons in length (where R' of 11, 13, 15 or 17 carbons in length are quite commonly employed).

Scheme I: Representative Reaction Between a FAME and a Dialcohol

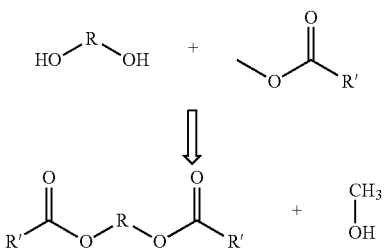

In one embodiment, provided is a method of producing a diol diester including reacting a mixture which includes a fatty acid methyl ester, an α,ω-alkanediol, wherein one more methylene units may be substituted by an oxygen atom, and a transesterification catalyst, wherein the mixture is reacted at a reaction temperature which is at least about 20° C. higher than the highest of the melting point of the diol diester, the melting point of the fatty acid methyl ester and 65° C.

The basic transesterification catalyst, if added, may be removed from the reaction mixture at the end of the reaction using suitable methods. Thus, in some embodiments, the method further includes diluting the first reaction product with an organic solvent to provide a diluted reaction product; and filtering the diluted reaction product to remove the basic transesterification catalyst.

In some embodiments, wherein the fatty acid alkyl ester includes one or more unsaturated fatty acid methyl esters, the method may further include hydrogenating the first reaction product.

In some embodiments, the first reaction product which includes the diol diester may be further processed to affect separation and purification of the diol diester. Thus, in one embodiment, the method further includes dissolving the diol diester in the first diol diester product in an organic solvent to provide a dissolved product mixture. In some embodiments, the organic solvent is an inert organic solvent. In some embodiments, the organic solvent includes, but is not limited to a halogenated aliphatic hydrocarbon, an alicyclic ether or an aromatic hydrocarbon. Suitable organic solvents include for example, dichloromethane(methylene chloride), trichloromethane, carbon tetrachloride, dichloroethane, trichloroethane, tetrachloroethane, pentachloroethane, chlorobenzene, benzene, toluene, acetone, and acethophenone, and the like or a combination of any two or more thereof. The diol diester in the first diol diester product may be dissolved in an organic solvent at room temperature or at elevated temperatures.

In some embodiments, the method further includes filtering the dissolved product mixture. In some embodiments, filtering the dissolved product mixture is slurried with a filtering aid. Suitable filtering aids include, for example, diatomaceous earth filter aids such as Celite® filter reagent (e.g., Celite® 545, Celite® 503 or Celite® 512), Perlite® filter reagent (e.g., Perlite® J-100, Hyflo-Super® (Hyflo Super-Cel®, Hyflo Super-eel®, Hyflo Super-Col®), cellulose filter aids (e.g., SolkaFloc® and Alpha-Cel®), or carbon-based filter aids. In some embodiments, the filtering aid is Celite.

In some embodiments, the method further includes purifying the diol diester using suitable purification methods. In some embodiments, the diol diester is purified by recrystallization using suitable solvents e.g., acetone.

In some embodiments, the reaction of a fatty acid alkyl ester with an α,ω-alkanediol reacting the mixture produces an alkanol and the method further includes continuously removing the alkanol from the reacting mixture. In some embodiments, the fatty acid alkyl ester is a fatty acid methyl ester; and the method further comprises removing methanol from the reaction mixture. The alkanol may be removed from the reaction mixture under vacuum. Thus, in some embodiments, the method further includes removing the methanol from the reaction mixture under vacuum.

In some embodiments, the FAAE used in the present methods may be derived from renewable plant and/or animal fats and oils. In some embodiments, the FAAE may be synthesized from a triglyceride-containing oil feedstock. In some embodiments, the FAAE may be prepared by the transesterification of a triglyceride containing feedstock. In some embodiments, the triglyceride containing feedstock does not contain substantial amounts of free fatty acids. In some embodiments, the FAAE may be prepared by the transesterification of a triglyceride containing biodiesel feedstock. In some embodiments, the FAAE may be prepared by the transesterification of a triglyceride containing feedstock with an alcohol, optionally in the presence of an esterfication catalyst. In some embodiments, the alcohol may be a lower alcohol. In some embodiments, the alcohol is methanol, ethanol, propanol, butanol or pentanol. In some embodiments, the alcohol is methanol. In some embodiments, the esterification catalyst is an acid catalyst, such as for example p-toluenesulfonic acid, phosphoric acid, polyphosphoric acid, phosphorous pentoxide, sulfuric acid, stannous chloride, hydrofluoric acid, and nitric acid, or solid acid catalysts like sulfonated zirconia, zirconium oxide/tungsten oxide catalyst, zeolites, acidic ion-exchange resins, and Nafion® acid resin. In other embodiments, the esterification catalyst is a base catalyst, selected from alkali metals, alkali metal carbonates, alkaline earth carbonates, alkali metal hydrides, alkaline earth hydrides, alkali metal alkoxides, and alkaline earth alkoxides. In some embodiments, the esterification catalyst is selected from sodium hydroxide, sodium methoxide potassium hydroxide and potassium carbonate. An exemplary synthesis of FAAE, e.g., FAME from triglyceride-containing feedstock is depicted in Scheme II.

Scheme II: Synthesis of FAME from a triglyceride

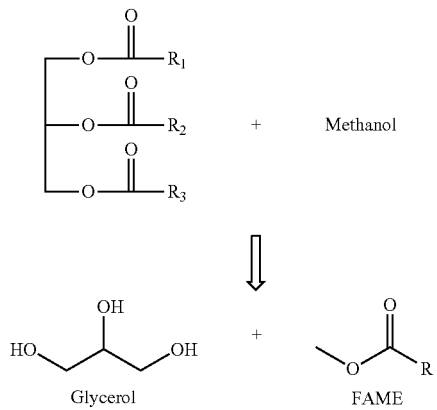

Glycerol     FAME

The diol diester compositions described herein provide excellent phase change materials and function over a wide range of working temperatures, whilst maintaining the amount of heat absorbed or released within a predictable range. The PCM materials described herein may be used in construction materials, thermal energy storage, shipping, storage or packaging materials, waste heat recovery, off peak power utilization, medical devices and articles, space exploration, computer/electrical component cooling, cosmetics and shampoo compositions, and clothing and textiles. Due to the non-toxic reactants and synthesis conditions, and the wide range of phase change temperatures, these materials can be safely used for food and beverage related applications.

The process presented herein creates longer chain fatty diesters from dialcohols and fatty acid derivatives. While not limiting the present invention, the presence of the ester groups is believed to enhance the enthalpy of the crystallized materials because of the interplay between the van der Waals and π-π electronic interactions; resulting in forces which lock the ester chain into a minimal energy conformation. The presence of both the hydrocarbon van der Walls and ester group π-π attraction forces is believed to result in a greater crystal lattice energy than experienced in the paraffin waxes, which lack π-π attraction forces. This may manifest itself in the greater enthalpy of crystallization and melt reported in the diester molecules. The PCMs described herein have been determined to have latent heat values between 230 and 260 J/g, and are 9-32% higher than the commercially available, petrochemically derived paraffin waxes, whose latent heats are greater than conventionally used PCMs such as paraffins. These PCMs therefore provide excellent latent heat storage materials.

Accordingly, in one aspect, provided herein is a latent heat storage article including a matrix material having a phase change material (PCM) embedded therein, wherein the PCM includes a diol diester having a melting point of about 30 to 90° C. and represented by a formula

wherein R—C(O)O— and R'—C(O)O— are fatty acid acyl groups and the R— and R'— groups independently have from 5 to 30 carbon atoms, and n is an integer from 2 to about 30, more commonly 2 to 22.

In some embodiments, the fatty acid acyl groups (also referred to herein as "fatty acyl groups") in the PCM are a C6-C22 saturated and/or unsaturated fatty acid. In some embodiments, the fatty acyl groups are a C10-C18 saturated and/or unsaturated fatty acid. In some instances, the fatty acyl groups may be a C16 and/or C18 fatty acyl group while n is 2, 3 and/or 4. In other embodiments, the fatty acyl groups may be a C18 acyl group (e.g., a stearate and/or oleate group) and n is 5, 7 and/or 9. In other embodiments, the fatty acyl groups may be a C18 acyl group and n is 2. In other embodiments, the fatty acyl groups may be a C18 acyl group and n is 4. In other embodiments, the fatty acyl groups may be a C16 acyl group (e.g., a palmitate group) and n is 4. In some embodiments, the fatty acyl groups may be a C16 acyl group and n is 2.

In some embodiments, the fatty acyl groups include one or more saturated fatty acyl groups. In some embodiments, the fatty acyl groups may include one or more unsaturated fatty acyl groups. In some instances, the fatty acyl groups correspond to the fatty acid the fatty acid composition of a vegetable oil or fraction thereof. For example, the vegetable oil may include soybean oil, palm oil, corn oil, cottonseed oil, sunflower oil, canola oil and/or coconut oil. In some embodiments, the fatty acyl groups acyl group may correspond to the fatty acid composition of a hydrogenated (either partially or completely hydrogenated) vegetable oil or fraction thereof.

The mixture of fatty acids isolated from complete hydrolysis of a fatty acid ester material, such as a triacylglyceride material (e.g., a vegetable oil, tallow or a fraction therefor), in a specific sample are referred herein to as the "fatty acid composition" of that sample. By the term "fatty acid composition" reference is made to the identifiable fatty acid residues in the various esters. The distribution of fatty acids in a particular triacylglyceride oil or other fatty ester mixture may be readily determined by methods well known to those skilled in the art, e.g., via gas chromatography or complete conversion to a mixture of fatty acid methyl esters followed by analysis by gas chromatography.

In some embodiments, the fatty acyl groups are stearate groups. Such PCMs may include a diol diester, which has a peak melting point of at least about 60° C. and/or a latent heat enthalpy of at least about 230 kJ/kg.

In some embodiments, the fatty acyl groups are palmitate groups. Such PCMs may include a diol diester, which has a peak melting point of at least about 55° C. and/or a latent heat enthalpy of at least about 230 kJ/kg.

The value of the integer n and correspondingly the properties of the resulting diol diester can be modulated by using alkane diols of varying chain length. In some embodiments, n is an integer from 2 to 22, from 2 to 20, from 2 to 15, from 2 to 12, from 2 to 10 or from 2 to 4. In some embodiments, n may be an odd number. In other embodiments, n may desirably be an even number (e.g., 2, 4, 6 or 8). In some embodiments, n may be 2. In many instances, embodiments where n is 2, 3 and/or 4, i.e., the diol is ethanediol, 1,3-propanediol and/or 1,4-butanediol maybe advantageously employed.

In some embodiments, n is an odd number, and the diol diester has a latent heat enthalpy of at least about 230 kJ/kg, or even a latent heat enthalpy about 250 kJ/kg or higher. In such embodiments, n may be 5, 7, 9 and/or 11.

The diol diester may include a compound represented by the formula

Me-(CH$_2$)$_x$—C(O)O—(CH$_2$)$_n$—OC(O)—(CH$_2$)$_x$-Me wherein x is an integer from 4 to 30 carbon atoms, commonly 8 to 16 carbon atoms; and n is an integer from 2 to 22, commonly 2 to 15. In some embodiments, the diol diester may consist essentially of a compound represented by this formula. In other embodiments, the diol diester may consist solely of a compound represented by this formula. The diol diester may have fatty acid acyl groups which include stearate groups (x is 16). Such diol diesters may have a peak melting point of at least about 60° C. and a latent heat enthalpy of at least about 225 kJ/kg. In some aspects, the PCM consists of diol diesters wherein x is 14 and/or 16, and n is 2, 3 and/or 4. In some aspects, the PCM consists of diol diesters wherein x is 14 and/or 16, and n is 2. In some aspects, the PCM consists essentially of and may consist solely of diol diesters wherein x is 16 and n is 5, 7 or 9. In other instances, the PCM consists essentially of and may consist solely of a diol diester in which x is 16 and n is 2 (a "18-2-18 diol diester"). In other instances, the PCM consists essentially of and may consist solely of a diol diester in which x is 16 and n is 4 (a "18-4-18 diol diester"). In other instances, the PCM consists essentially of and may consist solely of a diol diester in which x is 14 and n is 2 (a "16-2-16 diol diester"). In other instances, the PCM consists essentially of and may consist solely of a diol diester in which x is 14 and n is 4. (a "16-4-16 diol diester").

In many embodiments, it may be advantageous to employ a PCM which is quite pure and includes a relatively high percentage of the diol diester. The PCM typically includes at least about 90 wt. % of the diol diester and may include, at least about 92 wt. %, at least about 95 wt. %, at least about 96 wt. %, at least about 98 wt. %, or at least about 99 wt. %, of the diol diester. It has been found that the patent heat enthalpy of highly pure samples of the diol diester have substantially higher latent heat enthalpies than previously reported for such compounds. The diol diester may have a latent heat enthalpy of at least about 225 kJ/kg. More commonly, the present PCM has a latent heat enthalpy of at least about 230 kJ/kg, at least about 240 kJ/kg, or at least about 250 kJ/kg. In some embodiments, the PCM includes at least about 98 wt. % of the diol diester, which has a latent heat enthalpy of at least about 230 kJ/kg. In such embodiments, diol diester may have a latent heat enthalpy of at least about 240 kJ/kg.

In many embodiments, the PCM has a latent heat enthalpy of at least about 200 kJ/kg. PCM has a latent heat enthalpy of at least about 200 kJ/kg. More commonly, the present PCM has a latent heat enthalpy of at least about 225 kJ/kg, at least about 230 kJ/kg, at least about 240 kJ/kg, or at least about 250 kJ/kg. In some embodiments, the PCM includes at least about 98 wt. % of the diol diester and has a latent heat enthalpy of at least about 230 kJ/kg.

In some embodiments, the purity of the diol diester may be determined by derivative thermogravimetric analysis. Advantageously, the PCM includes a diol diester, for which derivative thermogravimetric analysis demonstrates that the diol diester does not exhibit a thermal degradation peak below 300° C. It has been found that the presence of impurities characterized by a thermal degradation peak below 300° C. in a particular sample of a diol diester can lead to substantially lowering of the latent heat enthalpy of such a material.

In some embodiments, provided herein is a latent heat storage article including a matrix material having a phase change material (PCM) embedded therein. Examples include construction materials, such as concrete or gypsum wall board, having the PCM embedded therein. The phase change material embedded in the matrix may be encapsulated in a suitable substrate material. In some embodiments, the phase change material is encapsulated in a polymer shell. In other embodiments, the phase change material is encapsulated in a metallic shell.

In some embodiments, provided herein is a latent heat storage unit including a PCM in thermal contact with a fluid conduit passing through the unit. For example, the latent heat storage unit may be part of a compressed air energy storage (CAES) system, where the PCM is used to cool compressed air flowing through the fluid conduit as well as store thermal energy for later use. The PCM typically comprises a diol diester represented by a formula:

R—C(O)O—(CH$_2$)$_n$—OC(O)—R' wherein the R—C(O)O— and R'—C(O)O— groups are fatty acid acyl groups and the R— and R'— groups independently have from 5 to 30 carbon atoms; and n is an integer from 2 to about 30, more commonly 2 to 22. The PCM may comprise a diol diester represented by a formula:

Me-(CH$_2$)$_x$—C(O)O—(CH$_2$)$_n$—OC(O)—(CH$_2$)$_x$-Me wherein x is an integer from 6 to 30 carbon atoms (typically 8 to 16), and n is an integer from 2 to 22 (typically 2 to 10). Various embodiments of the latent heat storage article may employ any of the diol diesters described herein. In some embodiments, the PCM may be dispersed in a thermal transfer fluid in thermal contact with the fluid conduit.

The present invention, thus generally described, will be understood more readily by reference to the following examples, which are provided by way of illustration and are not intended to be limiting of the present invention.

EXAMPLES

Example 1

Synthesis of Diol Diesters 20 even and 4 odd carbon length diesters were synthesized in small scale for screening as PCMs using a previously published method described in Floros M. C., Narine S. S., *Materials Letters*. 2014; 137:252-5. Base catalyzed diester synthesis in larger scale reactions are described with a novel method utilizing KOH or $K_2CO_3$ catalyzed transesterification. 5 even lengthened diesters (16-n-16, where n=2, 4, 6, 8, and 10 carbon atoms) were synthesized from methyl palmitate (n=16) in a larger scale 'green' synthesis for proof of concept. This method is represented herein as a prescriptive method for the synthesis of the diol diester 16-4-16 (Scheme III).

which removed the filter reagent and residual catalyst, rendering the product clear and colourless. The product was further purified by recrystallized from hot acetone, and finally dried under reduced pressure to yield 41.5 g of large white crystals in a 72.2% yield.

$^1$H NMR (500 MHz, $CDCl_3$) δ ppm 0.88 (t, 6H, —$CH_2$—$CH_3$) 1.17-1.41 (m, 48H, —R—$CH_2$—R) 1.58-1.67 (m, 4H, —$CH_2$—$CH_2$—COO—) 1.67-1.81 (m, 4H, —COO—$CH_2$—$CH_2$—$CH_2$—$CH_2$—COO—) 2.30 (t, J=7.63 Hz, 4H, —$CH_2$—$CH_2$—COO—) 4.00-4.23 (m, 4H, —COO—$CH_2$—).

Similar yields could be obtained using $K_2CO_3$ for dialcohols up to 4 carbons in length, however, longer carbon chain dialcohols provided lower yields unless higher reaction temperatures and longer reaction times were employed.

Example 2

Characterization of Synthesized Diol Diesters

Structures were confirmed by $^1$H NMR recorded on a Varian Unity-INOVA at 499.695 MHz in $CDCl_3$ at room temperature and a sample spin rate of 20 Hz (Agilent Technologies, Santa Clara, Calif., USA). Calorimetry studies were performed on a DSC Q200 (TA Instruments, Newcastle, Del., U.S.A.) equipped with a refrigerated cooling system. Each sample (4-8 mg), in a hermetically sealed Scheme III: Synthesis of 16-4-16 from methyl palmitate and 1,4-butanediol

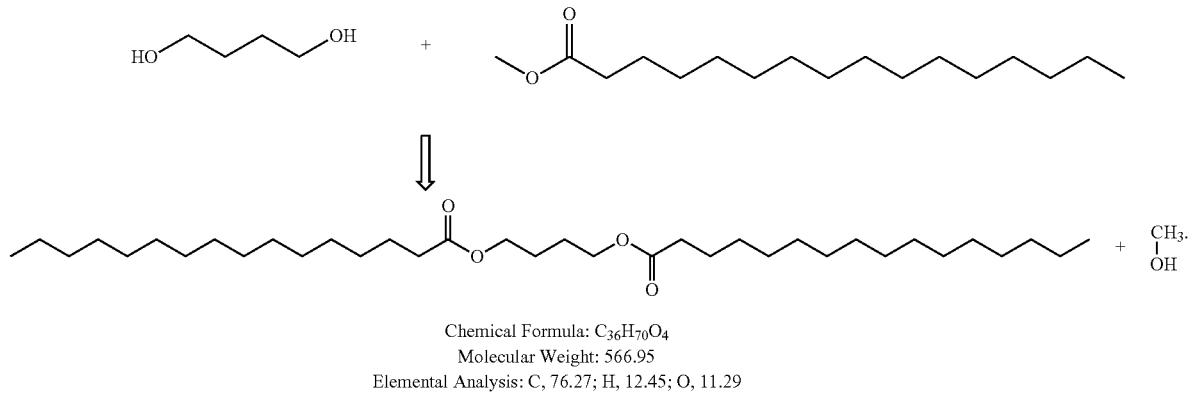

Chemical Formula: $C_{36}H_{70}O_4$
Molecular Weight: 566.95
Elemental Analysis: C, 76.27; H, 12.45; O, 11.29

A 100 mL round bottom flask was charged with 54.8 g methyl palmitate and heated to 120° C. 0.27 g of KOH was crushed into a fine powder and added to the heated methyl palmitate and the mixture was stirred until it became a homogeneous phase. The amount of KOH used was approximately 0.1% of the methyl ester, by mass. 9.13 g of 1,4-butanediol was slowly added to the reaction mixture. Methanol formed during the reaction was rapidly evolved under atmospheric pressure, and further evacuated by connecting the flask to a vacuum line. After the evolution of methanol was no longer detected (approximately 1 hour), the reaction mixture was allowed to cool. The crude product, which was slightly yellow in colour and cloudy, was dissolved in hot acetone and stirred with approximately 1 gram of celite filter reagent. After 5 minutes, this solution was vacuum filtered through a glass funnel with a sintered disk, pan, was heated to 100° C. and held for 5 min to erase thermal history, then cooled at a rate of 3.0° C./min down to 0° C. where it was held isothermally for 5 min. Finally the sample was heated from 0° C. to 100° C. at a rate of 3.0° C./min.

After recrystallization and drying overnight in a vacuum oven, NMR spectra of the samples (Table 1 and 2) were obtained to ensure the desired structure was obtained. If the spectra contained any evidence of impurities, such as residual methyl esters (characteristic shift at δ 3.67 ppm, s), acid chlorides (characteristic shift at δ 2.88 ppm, t 2H), monohydroxy esters (characteristic shifts at δ ~3.70 ppm, br) or other unassigned peaks, an additional recrystallization was performed and the NMR spectra was obtained and reanalyzed. Only once the samples were determined to be pure were analyses conducted.

TABLE 1

16-n-16 diesters produced by the FAME transesterification method.

| Chemical name: | Synonym: | $^1$H NMR (δ ppm): | Yield (%) |
|---|---|---|---|
| Ethane-1,2-diyl dihexadecanoate | 16-2-16 | δ 0.88 (t, 6 H) 1.21-1.45 (m, 48 H) 1.58-1.70 (m, 4 H) 2.32 (t, J = 7.57 Hz, 4 H) 4.27 (s, 4 H) | 70 |
| Butane-1,4-diyl dihexadecanoate | 16-4-16 | δ 0.88 (t, 6 H) 1.19-1.42 (m, 56 H) 1.59-1.66 (m, 4 H) 1.66-1.77 (m, 4 H) 2.29 (t, J = 7.57 Hz, 4 H) 4.01-4.21 (m, 4 H) | 72 |
| Hexane-1,6-diyl dihexadecanoate | 16-6-16 | δ 0.88 (t, 6 H) 1.11-1.34 (m, 48 H) 1.38 (m, J = 7.45, 3.85 Hz, 4 H) 1.57-1.72 (m, 8 H) 2.21-2.37 (m, 4 H) 4.06 (t, J = 6.59 Hz, 4 H) | 77 |
| Octane-1,8-diyl dihexadecanoate | 16-8-16 | δ 0.88 (t, 6 H) 1.19-1.43 (m, 56 H) 1.61 (t, J = 6.84 Hz, 8 H) 2.29 (t, J = 7.57 Hz, 4 H) 4.05 (t, J = 6.59 Hz, 4 H) | 63 |
| Decane-1,10-diyl dihexadecanoate | 16-10-16 | δ 0.88 (t, 6 H) 1.21-1.37 (m, 60 H) 1.58-1.69 (m, 8 H) 2.29 (t, J = 7.57 Hz, 4 H) 4.05 (t, J = 6.59 Hz, 4H) | 78 |

TABLE 2

Even carbon number diesters synthesized for screening by the present method

| Chemical name: | Synonym: | $^1$H NMR (δ ppm): |
|---|---|---|
| Ethane-1,2-diyl dioctadecanoate | 18-2-18 | δ 0.88 (t, 6 H) 1.17-1.39 (m, 56 H) 1.56-1.68 (m, 4 H) 2.32 (t, J = 7.45 Hz, 4 H) 4.27 (s, 4 H) |
| Butane-1,4-diyl dioctadecanoate | 18-4-18 | δ 0.89 (t, 6 H) 1.24-1.33 (m, 56 H) 1.56-1.65 (m, 4 H) 1.69-1.73 (m, 4 H) 2.30 (t, J = 7.63 Hz, 4 H) 4.08-4.12 (m, 4 H) |
| Hexane-1,6-diyl dioctadecanoate | 18-6-18 | δ 0.88 (t, 6 H) 1.18-1.35 (m, 56 H) 1.38 (t, J = 3.66 Hz, 6 H) 1.62 (m, 8 H) 2.29 (t, J = 7.57 Hz, 4 H) 4.06 (t, J = 6.59 Hz, 4 H) |
| Octane-1,8-diyl dioctadecanoate | 18-8-18 | δ 0.86-0.90 (t, 6 H) 1.21-1.36 (m, 64 H), 1.61 (m, 8 H) 2.29 (t, J = 7.32 Hz, 4 H) 4.05 (t, J = 6.84 Hz, 4 H) |
| Decane-1,10-diyl dioctadecanoate | 18-10-18 | δ 0.88 (t, 6 H) 1.23-1.35 (m, 68 H) 1.56-1.65 (m, 8 H) 2.29 (t, J = 7.57 Hz, 4 H) 4.05 (t, J = 6.71 Hz, 4 H) |
| Ethane-1,2-diyl dihexadecanoate | 14-2-14 | δ ppm 0.88 (t, 6 H) 1.22-1.35 (m, 40 H) 1.58-1.67 (m, 4 H) 2.32 (t, J = 7.32 Hz, 4 H) 4.27 (s, 4 H) |
| Butane-1,4-diyl ditetradecanoate | 14-4-14 | δ 0.88 (t, 6 H) 1.22-1.39 (m, 40 H) 1.57-1.66 (m, 4 H) 1.66-1.76 (m, 4 H) 2.29 (t, J = 7.57 Hz, 4 H) 4.06-4.15 (m, 4 H) |
| Hexane-1,6-diyl ditetradecanoate | 14-6-14 | δ 0.88 (t, 6 H) 1.23-1.33 (m, 40 H) 1.33-1.43 (m, 4 H) 1.57-1.67 (m, 8 H) 2.29 (t, J = 7.57 Hz, 4 H) 4.04-4.09 (t, 4 H) |
| Octane-1,8-diyl ditetradecanoate | 14-8-14 | δ 0.88 (m, 6 H) 1.23-1.38 (m, 48 H) 1.57-1.66 (m, 8 H) 2.29 (t, J = 7.57 Hz, 4 H) 4.05 (t, J = 6.84 Hz, 4 H) |
| Decane-1,10-diyl ditetradecanoate | 14-10-14 | δ 0.88 (m, 6 H) 1.23-1.37 (m, 52 H) 1.56-1.66 (m, 8 H) 2.29 (t, J = 7.57 Hz, 4 H) 4.05 (t, J = 6.59 Hz, 4 H) |
| Ethane-1,2-diyl didodecanoate | 12-2-12 | δ 0.88 (t, J = 7.08 Hz, 6 H) 1.18-1.42 (m, 32 H) 1.62 (quin, J = 7.32 Hz, 4 H) 2.32 (t, J = 7.57 Hz, 4 H) 4.27 (s, 4 H) |
| Butane-1,4-diyl didodecanoate | 12-4-12 | δ 0.88 (t, 6 H) 1.16-1.38 (m, 32 H) 1.61 (quin, J = 7.32 Hz, 4 H) 1.66-1.78 (m, 4 H) 2.21-2.40 (m, 4 H) 3.99-4.15 (m, 4 H) |
| Hexane-1,6-diyl didodecanoate | 12-6-12 | δ 0.88 (t, 6 H) 1.21-1.34 (m, 32 H) 1.35-1.45 (m, 4 H) 1.58-1.73 (m, 8 H) 2.29 (t, J = 7.57 Hz, 4 H) 4.06 (t, J = 6.59 Hz, 4 H) |
| Octane-1,8-diyl didodecanoate | 12-8-12 | δ 0.88 (t, 6 H) 1.23-1.37 (m, 40 H) 1.55-1.65 (m, 8 H) 2.27-2.31 (t, 4 H) 4.05 (t, J = 6.59 Hz, 4 H) |
| Decane-1,10-diyl didodecanoate | 12-10-12 | δ 0.88 (t, 6 H) 1.22-1.38 (m, 44 H) 1.57-1.67 (m, 8 H) 2.29 (t, J = 7.57 Hz, 4 H) 4.03-4.09 (m, 4 H) |

FIG. 1a show the peak melting temperatures of the series of saturated diesters. Melting temperatures for this series range from 39 to 77° C. and demonstrate a trend wherein diesters with the dialcohol n=2 show the highest and n=6 the show the lowest melting points for each fatty acid. As the two outside groups on the diester increase in chain length from 12 through 18 carbon atoms, their melting points increase as well. Furthermore, in the both the odd and even diester series, dialcohols with the lowest (n=2 and n=3) and highest number (n=9 and n=10) of n carbons have the highest melting points, and diesters with n=5 for the odd series and n=6 for the even series have the lowest melting temperatures. A possible explanation for this is that when n is sufficiently small, stearic hindrance between the two ester groups within a diester hinders its free rotation about the COO—$CH_2$ bonds. This behaviour has been explained in detail for dicarboxylic acids, and takes note of extensive crystallography data, as well as computational simulation. A "Paralleloram-Trapezoidal Model" for describing the geometric modifications which occur in odd carbon numbered diacids has been reported. This model may also used to explain polymorphic behaviour, which was only present in the odd series. In the significantly larger molecules described in this study, as the number of carbon atoms, n, between the diesters is increased, the degree of stearic hindrance is reduced due to a greater separation between the esters. This is believed to result in the melting point becoming more dependent on the absolute molecular weight of a molecule, and consequently the sum of possible intermolecular interactions, as is seen in linear paraffins, which contain only carbon-carbon single bonds.

Latent heat values (FIG. 1b) range between 230 and 260 J/g, indicating these materials have high energy storage densities. These values are superior to the performance of paraffin wax, which is the most commonly used PCM in these temperature ranges, with reported latent heats between 189 and 210 J/g. The temperature range of this series of PCMs is ideal for applications such as thermal regulation of hot food and beverages, with the high latent heat values for also potentially qualifying them for applications requiring the storage of large quantities of thermal energy.

The present invention, thus generally described, will be understood more readily by reference to the preceding examples, which are provided by way of illustration and are not intended to be limiting of the present invention.

While certain embodiments have been illustrated and described, it should be understood that changes and modifications may be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. As will also be understood by one skilled in the art all language such as "up to," "at least," "greater than," "less than," and the like, include the number recited.

As used herein, "about" will be understood by persons of ordinary skill in the art and will vary to some extent depending upon the context in which it is used. The term "about" when used before a numerical designation, e.g., temperature, time, amount, and concentration, including range, indicates approximations which may vary by ±10%.

The use of the terms "a" and "an" and "the" and similar referents in the context of describing the elements (especially in the context of the following claims) are to be construed to cover both the singular and the plural, unless otherwise indicated herein or clearly contradicted by context. All methods described herein may be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated.

What is claimed is:

1. A method of producing a diol diester comprising reacting:
    a fatty acid alkyl ester having 6 to 30 carbon atoms;
    an α,ω-alkanediol having n carbon atoms, wherein n is an integer from 2 to 22; and
    about 0.01 to 1.0 wt. % (based on the weight of the mixture) of a basic transesterification catalyst;
    wherein the mixture is reacted at a reaction temperature of at least about 60° C. to provide a first reaction product comprising the diol diester; and
    the method further comprises recrystallizing the idol diester produced by the reaction.

2. The method of claim 1 further comprising diluting the first reaction product with an organic solvent to provide a diluted reaction product; and filtering the diluted reaction product to remove the basic transesterification catalyst.

3. The method of claim 1 further comprising dissolving the diol diester in the first diol diester product in an organic solvent to provide a dissolved product mixture; and filtering the dissolved product mixture.

4. The method of claim 3 wherein filtering the dissolved product mixture comprises filtering the dissolved product mixture slurried with a filtering aid.

5. The method of claim 1 wherein reacting the mixture produces an alkanol and the method further comprises continuously removing the alkanol from the reacting mixture.

6. The method of claim 1 wherein the mixture includes the fatty acid alkyl ester and the α,ω-alkanediol in a mole ratio of about 2:1 to 5:1.

7. The method of claim 1 wherein the mixture is substantially free of solvent.

8. The method of claim 1 wherein the basic transesterification catalyst is an inorganic basic compound.

9. The method of claim 1 wherein the basic transesterification catalyst is an alkali metal hydroxide, an alkali metal alkoxide and/or alkali metal carbonate.

10. The method of claim 1 wherein the fatty acid alkyl ester is a fatty acid methyl ester having 7 to 23 carbon atoms; the α,ω-alkanediol has 2 to 22 carbon atoms; and the basic transesterification catalyst comprises an alkali metal hydroxide and/or alkali metal carbonate.

11. The method of claim 1 wherein the basic transesterification catalyst is potassium hydroxide.

12. The method of claim 1 wherein the basic transesterification catalyst is potassium carbonate.

13. The method of claim 1 wherein the fatty acid alkyl ester is a fatty acid methyl ester; and the method further comprises removing methanol from the reacting mixture.

14. The method of claim 13 comprising removing the methanol from the reaction mixture under vacuum.

15. The method of claim 1 wherein the fatty acid alkyl ester is a fatty acid methyl ester; and the method comprises reacting the mixture at a temperature of about 90° C. to 150° C.

16. The method of claim 1 wherein the fatty acid alkyl ester is a methyl ester of a fatty acid having an even number of carbon atoms.

17. The method of claim 1 wherein the fatty acid alkyl ester comprises one or more saturated fatty acid methyl esters.

18. The method of claim 1 wherein the fatty acid alkyl ester comprises one or more unsaturated fatty acid methyl esters.

19. The method of claim 1 wherein the α,ω-alkanediol is ethanediol; 1,3-propanediol and/or 1,4-butanediol.

20. A method of producing a diol diester comprising reacting:
    a fatty acid alkyl ester having 6 to 30 carbon atoms; wherein the fatty acid alkyl ester comprises one or more unsaturated fatty acid methyl esters;
    an α,ω-alkanediol having n carbon atoms, wherein n is an integer from 2 to 22; and
    about 0.01 to 1.0 wt.% (based on the weight of the mixture) of a basic transesterification catalyst;
    wherein the mixture is reaction temperature of at least about 60° C. to provide a first reaction product comprising the diol diester; and the method further comprises hydrogenating the first reaction product.

21. A method of producing a diol diester consisting essentially of reacting:
    an aliphatic carboxylic acid alkyl ester having 6 to 30 carbon atoms,
    an α,ω-alkanediol having n carbon atoms, wherein n is an integer from 2 to 22, and
    about 0.01 to 1.0 wt.% (based on the total weight of the starting mixture) of a basic transesterification catalyst;
    wherein the reaction is conducted at a reaction temperature of at least about 60° C. to provide a first reaction product comprising the diol diester while substantially removing alkanol from the reacted mixture via distillation; and (c) diluting the reacted mixture with a solvent to form a product solution;

(d) filtering the product solution to remove the basic transesterification catalyst and provide a filtered solution; and (e) recrystallizing the diol diester from the filtered solution to provide a recrystallized diol diester.

22. The method of claim 21 wherein filtering the product solution comprises filtering the product solution slurried with a filtering aid.

23. The method of claim 21 wherein the recrystallized diol diester does not exhibit a thermal degradation peak below 300° C. as determined by derivative thermogravimetric analysis.

24. The method of claim 21 wherein the recrystallized diol diester has a peak melting point of at least about 60° C.

25. The method of claim 21 wherein the recrystallized diol diester has a peak melting point of at least about 60° C. and a latent heat enthalpy of at least about 225 kJ/kg and does not exhibit a thermal degradation peak below 300° C. as determined by derivative thermogravimetric analysis.

26. The method of claim 25 wherein the aliphatic carboxylic acid alkyl ester is a methyl ester of a fatty acid having 16 and/or 18 carbon atoms; and the α,ω-alkanediol has 5, 7 or 9 carbon atoms.

\* \* \* \* \*

UNITED STATES PATENT AND TRADEMARK OFFICE
CERTIFICATE OF CORRECTION

PATENT NO. : 9,434,674 B2
APPLICATION NO. : 14/605344
DATED : September 6, 2016
INVENTOR(S) : Suresh S. Narine and Michael C. Floros It is certified that error appears in the above-identified patent and that said Letters Patent is hereby corrected as shown below:

Claims

In column 15, line 55, Claim 1, change --idol-- to diol

In column 16, line 54, Claim 20, insert --the mixture is reacted at a reaction temperature of--

Signed and Sealed this
Eighth Day of November, 2016

Michelle K. Lee
*Director of the United States Patent and Trademark Office*